United States Patent [19]

Daudt et al.

[11] Patent Number: 4,553,217
[45] Date of Patent: Nov. 12, 1985

[54] GLASSWARE GAUGING SYSTEM

[75] Inventors: Stephen W. Daudt, Longmont; George W. Gleason, Boulder; William C. Hermanson, Boulder; Arthur A. Olsen, Boulder, all of Colo.

[73] Assignee: Ball Corporation, Muncie, Ind.

[21] Appl. No.: 629,891

[22] Filed: Jul. 11, 1984

Related U.S. Application Data

[62] Division of Ser. No. 281,467, Jul. 8, 1981, Pat. No. 4,476,533.

[51] Int. Cl.$^4$ .................. G06F 15/20; G01B 11/00
[52] U.S. Cl. ................... 364/560; 364/473; 364/562; 250/224; 356/383; 356/384
[58] Field of Search ............... 364/473, 507, 551, 552, 364/560, 562, 564; 65/29, 158, 160, DIG. 13; 356/375-387, 237, 240, 428, 73; 250/223 B, 224

[56] References Cited

U.S. PATENT DOCUMENTS

| | | | |
|---|---|---|---|
| 3,682,554 | 8/1972 | Flaczynski | 356/383 |
| 3,737,856 | 6/1973 | Lehrer et al. | 250/560 |
| 3,819,918 | 6/1974 | Hale | 356/383 |
| 3,870,890 | 3/1975 | Binks et al. | 250/560 |
| 3,897,156 | 7/1975 | Chasson | 356/383 |
| 3,907,438 | 9/1975 | Holeman | 356/428 |
| 3,922,094 | 11/1975 | Colding et al. | 250/560 |
| 4,002,823 | 1/1977 | Van Oosterhout | 358/106 |
| 4,046,536 | 9/1977 | Smithgall, Sr. | 356/385 |
| 4,063,820 | 12/1977 | Borgese | 356/381 |
| 4,107,523 | 8/1978 | Corman | 250/223 B |
| 4,203,673 | 5/1980 | Buckson | 250/224 |
| 4,209,387 | 6/1980 | Scherf | 209/530 |
| 4,343,637 | 8/1982 | Shofner et al. | 65/29 |
| 4,368,641 | 1/1983 | McLeod, Jr. | 364/552 |
| 4,380,025 | 4/1983 | Deane | 358/106 |
| 4,402,721 | 9/1983 | Ericson et al. | 65/29 |
| 4,432,648 | 2/1984 | Musto et al. | 250/224 |

OTHER PUBLICATIONS

"Quality Control Do You Need an Electronic Bottle Inspector?", *Beverage World*, Feb. 1980, pp. 32, 33 and 63.

*Primary Examiner*—Gary Chin
*Attorney, Agent, or Firm*—Gilbert E. Alberding

[57] ABSTRACT

A non-contact optical gauger for measuring glassware articles of manufacture at the hot end of an individual section machine. As the manufactured glassware is being conveyed away from the individual section machine, a light beam is direct across its path. An array of photo-sensitive sensors and a microprocessor based electronic system interpret the light beam interruptions as measurement data which are stored and can be displayed as desired.

21 Claims, 23 Drawing Figures

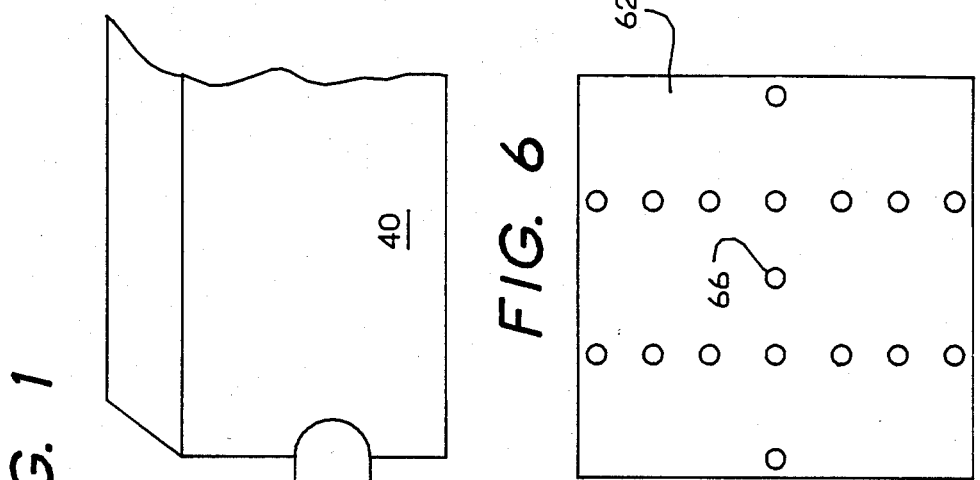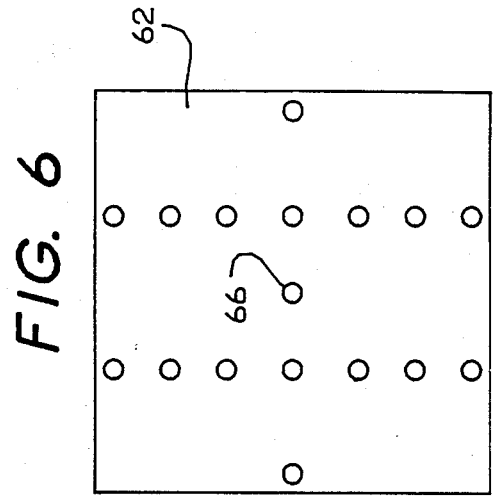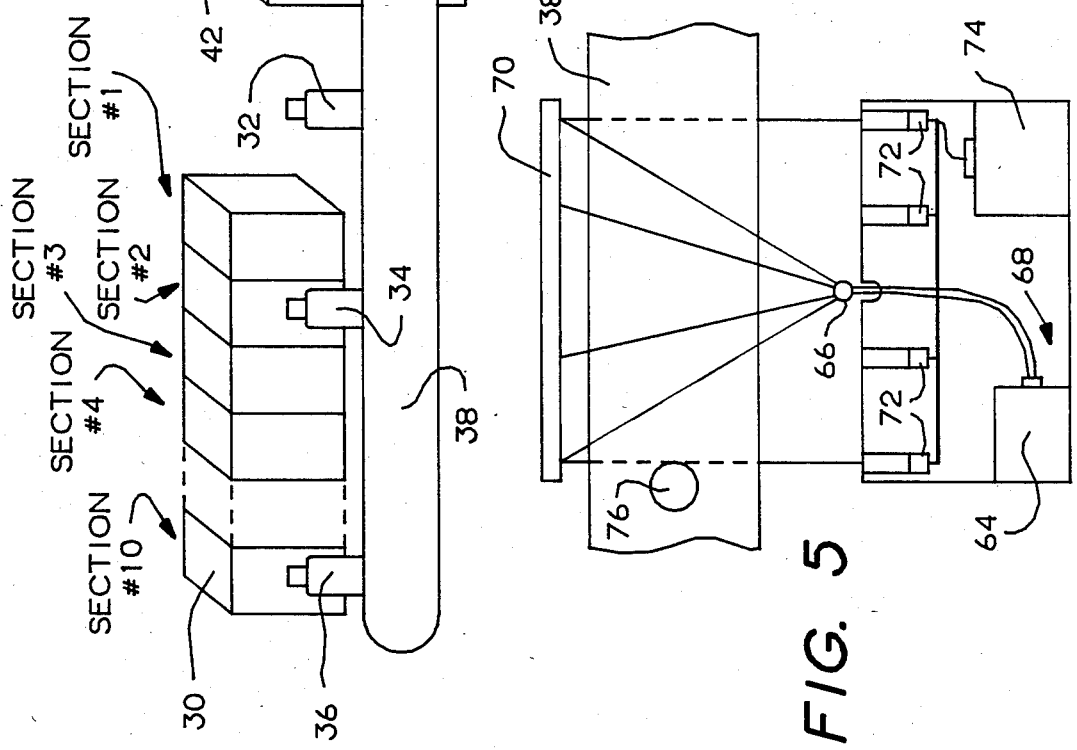

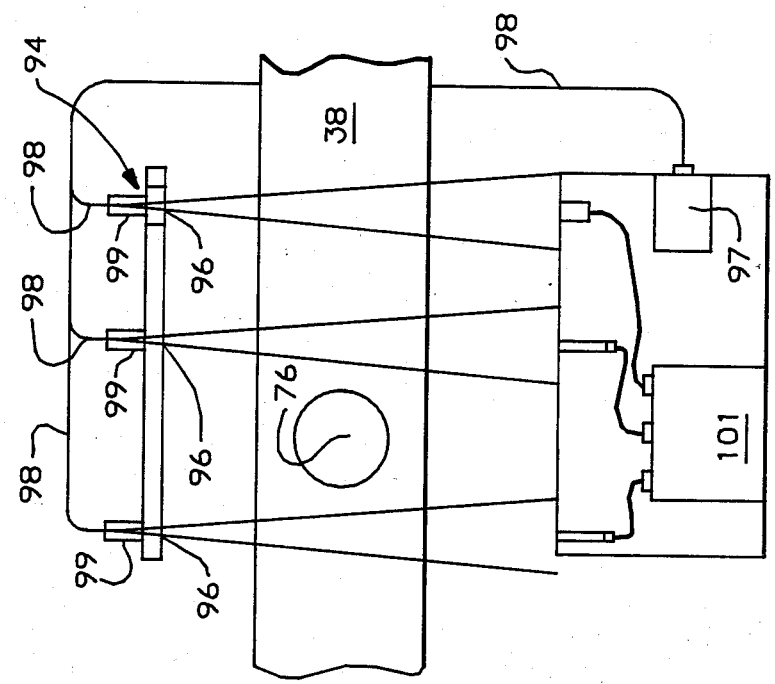
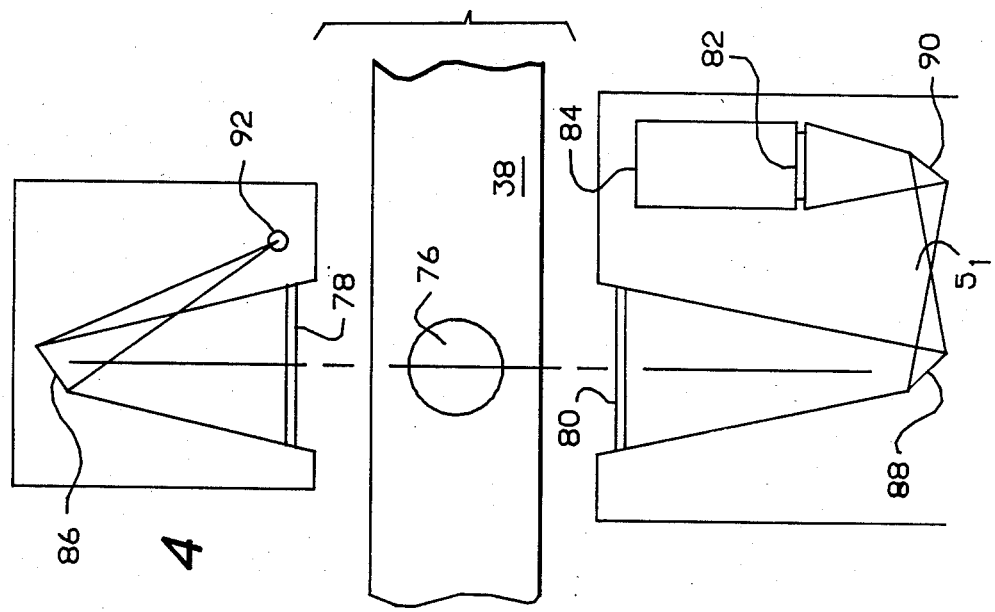

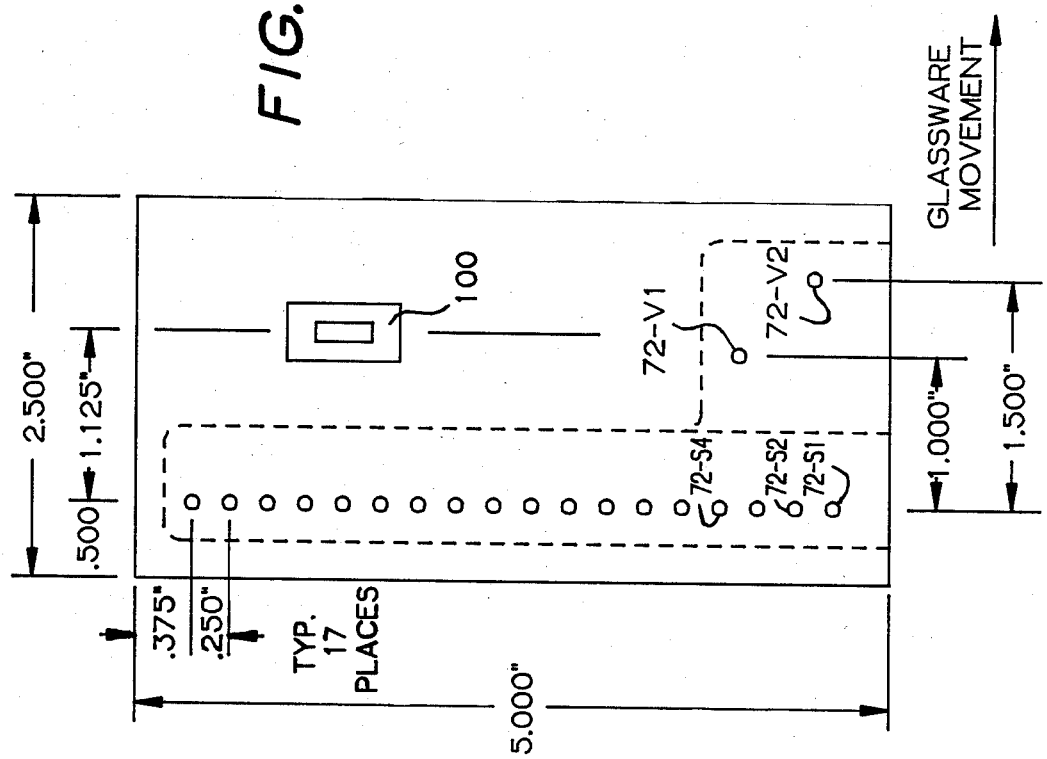

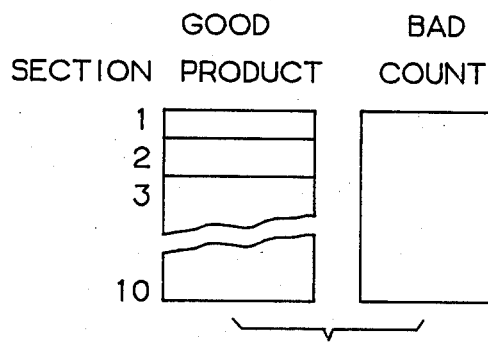
FIG. 14b
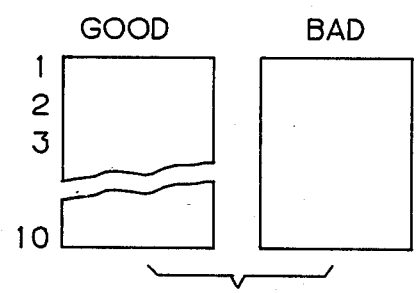
FIG. 14c
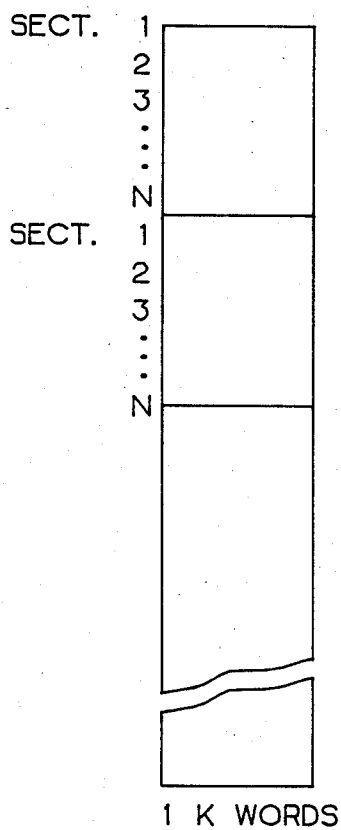
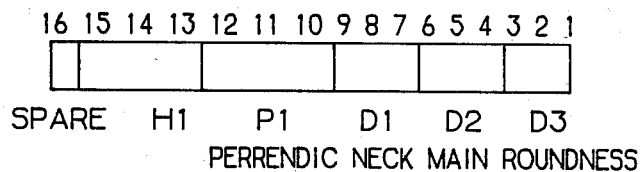
3 BIT CODE
1 LOW REJECT
2 LOW
3 GOOD
4 HIGH
5 HIGH REJECT
FIG. 14a

FIG. 17

GRAPH REPORT

| SEC. | R2345 | 12345 | 12345 | R2345 | R234R |
|---|---|---|---|---|---|
| 1 | 3 |   | 3 |   |   |
| 1 | 3 | 3 | 3 |   |   |
| 1 | 4 |   | 3 |   |   |
| 1 | 4 | 2 | 3 | 2 | 3 |
| 1 | 5 | 2 | 3 | 2 | 3 |
| 1 | 5 | 2 | 3 | 2 | 3 |
| 2 | 5 | 2 | 3 | 2 | 3 |
| 2 | 5 | 2 | 3 | R | R |
| 2 | 5 | 3 | 3 | 2 | 3 |
| 2 | 5 | 2 | 3 | R | 3 |
| 2 | 5 | 2 | 3 | 2 | 3 |
|   |   |   |   | R | 3 |
|   |   |   |   | R | 3 |

FIG. 18

RECORDS REPORT

| SEC. | H1 | P1 | REJECTS D1 | D2 | D3 | TOTAL REJECTS | GOOD PARTS |
|---|---|---|---|---|---|---|---|
| 1 | 0 | 0 | 0 | 0 | 0 | 0 | 2075 |
| 2 | 140 | 0 | 0 | 0 | 0 | 140 | 2080 |
| 3 | 1 | 7 | 0 | 0 | 0 | 8 | 1003 |
| 4 | 8 | 0 | 0 | 0 | 1 | 9 | 93 |
| 5 | 1 | 1 | 1 | 1 | 1 | 5 | 2076 |

4,553,217

GLASSWARE GAUGING SYSTEM

This application is a division, of application Ser. No. 281,467 now U.S. Pat. No. 4,476,533, filed July 8, 1981.

BACKGROUND OF THE INVENTION

The present invention relates in general to glassware manufacture. Specifically, this invention relates to apparatus and methods for measuring glassware. Even more specifically, this invention relates to non-contact means for measuring glassware at the hot end of a glassware production line.

A typical glassware manufacturing plant includes a forming machine, also known in the trade as an individual section or IS machine. A forming machine typically includes 6–10 identical individual sections for producing finished glassware such as bottles. A gob feeder mechanism common to all of the individual sections feeds a gob of molten glass to each of the sections of the forming machine in turn. Thus, at any point in time the glassware in each section of the forming machine is in a different state of completion from the glassware in every other section of the machine. As an article of glassware manufacture issues from each of the sections, it is carried by a conveyor, past an inspection area to a lehr. At the inspection area, the glassware articles of manufacture on the conveyor are inspected for flaws. This inspection may include the measurement of a representative sample removed from the conveyor. The flaw inspection is either accomplished by the actual observation of a human being stationed at the inspection area or by a video camera inspection system such as that set forth in U.S. Pat. No. 4,002,823. Another video camera inspection system for the detection of flaws is set forth in the co-pending patent application of David W. Deane filed on Aug. 6, 1979 and bearing Ser. No. 063,927 now Pat. No. 4,380,025 entitled VIDEO INSPECTION SYSTEM.

The inspection, carried out by an observer or by a video inspection system, generally looks for flaws such as spikes or bird swings within the finished glassware. Such inspections are not intended to provide for the measurement of each piece of glassware produced to insure that its dimensions fall within a predetermined tolerance.

In order to measure the glassware issuing from an individual section machine, it has been necessary to remove a sample of glassware from its conveyor, allow it to cool, and then measure its critical dimensions by hand. This is a somewhat clumsy and inefficient procedure. Thus, it would be highly advantageous to be able to automatically and accurately measure each piece of glassware produced by a forming machine during its conveyance to a lehr.

SUMMARY OF THE INVENTION

The present invention is directed to a non-contact arrangement for automatically measuring various critical dimensions of glassware suitable for use at the hot end of a glassware manufacturing line.

The presently preferred embodiment gauger according to the present invention includes a light source system for generating light on one side of the conveyor directed toward a sensing system positioned on the opposite side of the conveyor. Thus, glassware on the conveyor must pass through the light path from the light source system to the light sensing system.

The light sensing system includes an array of light sensitive elements onto which light from the light source system is focused by an optical system. The elements of the array generate electrical signals responsive to the light falling thereupon. An electronic system processes these electrical signals and interprets them as measurements of the dimensions of each piece of glassware.

Glassware article diameter measurements are made using a velocity dependent scheme. The article's velocity on the conveyor is determined by the time interval T that it takes for its leading edge to pass from a first position along the conveyor to a second position along the conveyor. This time interval T is sensed by counting clock pulses generated at a predetermined rate between signals generated by two separate light sensitive elements of the array that are spatially separated by a known distance S and are at an equal height above the conveyor. Once the velocity of a piece of glassware on the conveyor is known, a second time interval C during which a light sensitive element senses the presence of the glassware passing thereby is used to compute the diameter D measurement according to the formula $$D = \frac{C}{T} \times S$$

Article perpendicularity is measured by using a different pair of light sensitive elements within the array. Two elements, in vertical alignment with one another, sense the same edge of a piece of glassware as it passes a predetermined position along the conveyor. The edge time difference between a time A sensed by one sensor of the pair and a time B sensed by the other is used to measure the perpendicular offset of the glassware according to the formula:

$$\text{Perpendicular Offset} = \frac{(A - B)S}{T}$$

In order to measure the roundness of an article of glassware multiple views of the glassware are provided. The diameter of the article is measured from each view and these diameter measurements are compared. One technique for presenting these multiple views utilizes mirrors to provide multiple views from different angles. The mirrors are positioned about the conveyor so as to present multiple views of each article of glassware to a single gauger. Diameter measurements are taken from each view in succession. A comparison of these diameter measurements indicates the degree of roundness of the glassware.

A second technique for presenting these multiple views utilizes plural gaugers positioned about the conveyor so as to have different angular views of the article glassware. Each gauger measures body diameter of the article independently. These independent measurements are stored and then compared to establish the roundness of the article.

Measurements taken by the gauger are stored and then compared with measurement criteria. This comparison is used to generate a quality rating for each measurement. Measurements having a quality rating that indicates that the measurement falls outside of a minimum tolerance range trigger, a reject signal for actuating a reject valve between the forming machine and lehr so that defective articles, i.e., articles having a critical dimension outside of specified tolerance, are deflected before that particular article enters the lehr.

BRIEF DESCRIPTION OF THE DRAWINGS

Many of the attendant advantages and features of the present invention will be readily apparent as the invention becomes better understood by reference to the following detailed description along with the appended claims when considered in conjunction with the accompanying drawings wherein:

FIG. 1 is a pictorial diagram of the inspection line of a glassware manufacturing facility showing the relative position of the gauger according to the present invention.

FIG. 4 is a cut-away top pictorial view of the gauger according to the present invention using a Fresnel lens optical system and also showing a top view of the conveyor and a piece of glassware being measured.

FIG. 5 is a top cut-away pictorial view of an alternate optical system utilizing a mirror optical system.

FIG. 6 is a front view of a portion of the detector array positioned at the image plane of the gauger FIG. 7 is a top cut-away pictorial view of a second alternate optical system utilizing a fiber optic bundle.

FIG. 8 is a front view of the detector array positioned at the image plane of the gauger according to the present invention.

FIG. 9 is a side view of a typical bottle being measured by gauger 42 according to the present invention.

FIGS. 14a–14c are pictorial representations of various areas of memory of the electric signal processor and an illustrative code generated related to bottle measurement by the electronic signal processor.

FIG. 17 is a diagram of a graph report displaying data from memory representing bottle measurements; and FIG. 18 is a diagram of a records report generated with data from memory representing an entire production run for a forming machine.

DETAILED DESCRIPTION OF THE PREFERRED EMBODIMENT

Figure 2:
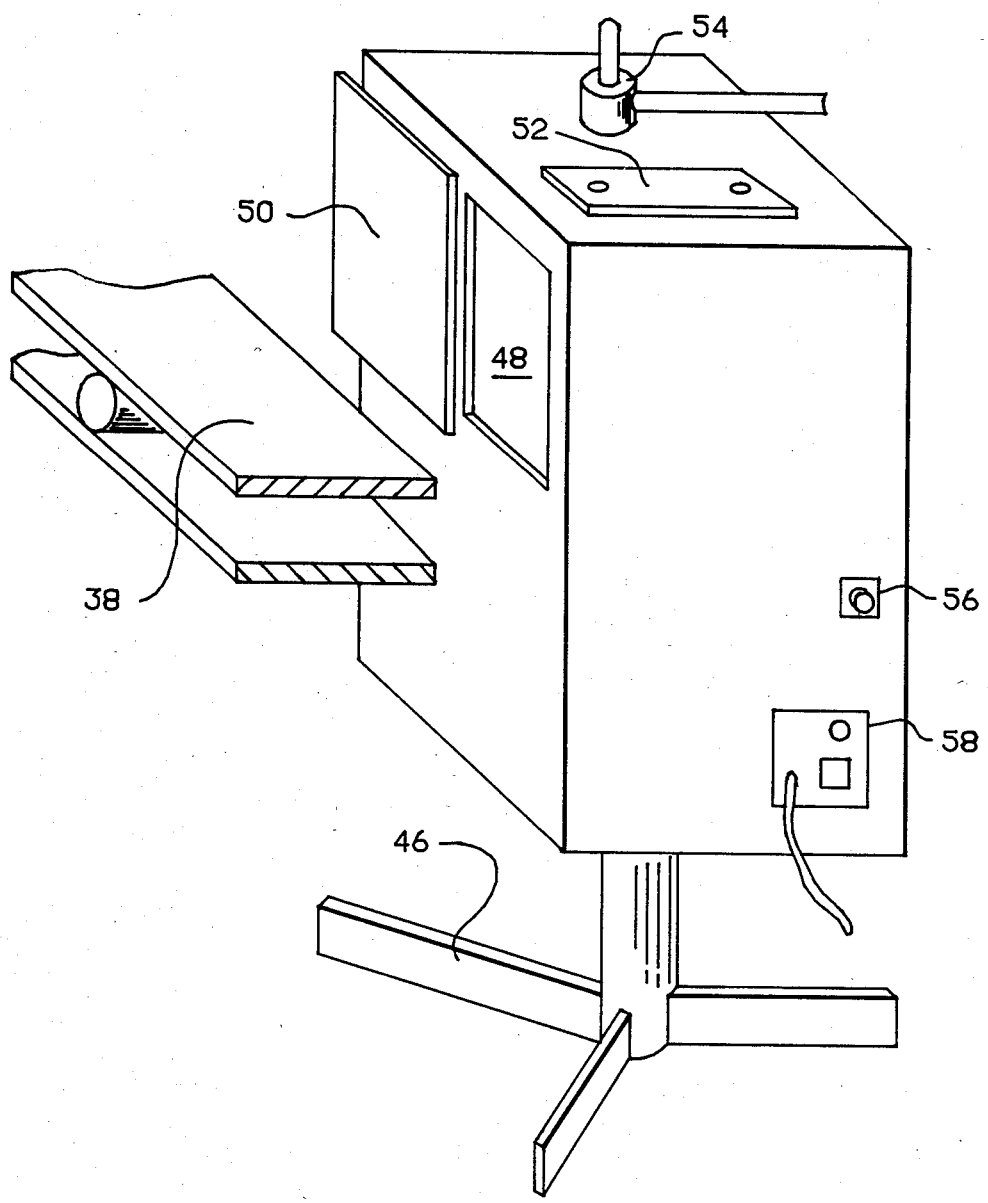
FIG. 2 is a perspective view of the gauger according to the present invention.

Referring now to the Figures wherein like reference numerals designate like or corresponding parts throughout the several views, and specifically referring to FIG. 1, there is shown a pictorial diagram of an inspection line of a typical glassware manufacturing facility.

A forming machine 30, also known as an individual section machine or IS machine includes multiple individual sections for producing finished glassware as represented by bottles 32, 34 and 36.

Forming machine 30 generally includes six to ten such individual identical sections. A ten section machine is represented pictorially in FIG. 1.

Forming machine 30 generally includes a gob feeder mechanism which feeds a gob of molten glass to each of the sections of the machine. This stream of molten glass in the gob feeder is cut by shears so that a measured portion of glass is fed to each of the individual sections of the forming machine. The gob feeder usually includes a chute from the source of molten glass to each of the sections.

Although the ten sections of forming machine 30 function simultaneously, the various sections are operated out of phase with respect to one another. In essence, the gob feeder mechanism feeds molten glass to each individual section in turn. Thus, at any particular time, the glassware in each section is in a different stage of completion. The sequencing of the gob feeder mechanism in feeding glass to each individual section establishes a forming machine clock rate. By knowing this clock rate and a boundary condition such as bottle 32 was produced by a section #6, it can be determined which section produced each of the bottles issuing from the machine. Thus, the measurements made by the gauger can be correlated with the sections of forming machine 30 producing the glassware articles. Gauger 42 can therefore be utilized in a feedback path supplying information to forming machine 30, causing its operation to be modified, as necessary.

Glassware articles such as bottles 32, 34 and 36 produced by the various sections of forming machine 30 are transported by a conveyor to a lehr 40. Along conveyor 38 and between forming machine 30 and lehr 40, there is positioned a gauger according to the present invention, generally referred to by reference numeral 42. Gauger 42 provides various measurements of the bottles passing by its field of view. Specific measurements of height, perpendicularity, neck diameter, body diameter, and height variation are determined and stored in memory for subsequent processing or display.

By utilizing multiple gaugers or by using a single gauger with external mirrors, multiple view diameter dimensions can be taken from which a measure of the roundness of the bottles can be determined. The measurements thus taken are rated against predetermined criteria and may be assigned a quality factor based upon deviation from the criteria. In addition, measurements falling outside of a minimum tolerance range for each category of measurement causes the activation of a reject plunger 44 for removing a defective (out of tolerance) piece of glassware from conveyor 38 before that piece would enter lehr 40. When a measurement is taken that is outside of a minimum tolerance range for that particular measurement, gauger 42 generates a signal causing reject plunger 44 to be activated at the appropriate time to remove the defective bottle from conveyor 38. The appropriate time for reject plunger activation can be determined based upon the distance of gauger 42 from reject plunger 44 and the velocity of conveyance of the glassware.

All measurements taken, whether outside of a minimum tolerance range so as to trigger reject plunger 44 or not, are rated against predetermined criteria. These ratings provide a measure of the quality of the bottles on conveyor 38. The clock rate of forming machine 30 and the particular section of forming machine 30 that produced a particular bottle is known and a correlation is established between each piece of glassware and the particular section producing it. Thus, data is available for use on-the-spot adjustment of a particular section of forming machine 30. Such data can be printed in an easy to interpret form such as the tables shown in FIGS. 17 and 18, discussed below.

Referring now to FIG. 2, there is shown a perspective view of a portion of gauger 42 according to the present invention. As is apparent from this figure, it is intended that gauger 42 be free standing and not make any contact with the bottles being measured. Gauger 42 includes a mounting stand 46, the height of which is adjustable so that the gauger can be positioned adjacent conveyor 38 regardless of the height of the conveyor. A viewing window 48 provides a portal for optical measurements to be taken of the bottles being transported by conveyor 38. A slidable cover 50 can close off window 48 during periods of non-use. A bracket 52 provides a convenient point from which to cantilever mount the light source system on the opposite side of conveyor 38 from the sensing system. A vortex cooling arrangement 54 provides for heat dissipation from gauger 42. An output terminal 56 provides a means for coupling to reject plunger 44 so that a signal can be coupled thereto when gauger 42 determines that a particular bottle has been measured to be outside of minimum tolerance range. Gauger 42 is powered by standard 115 volt AC power coupled through a power input terminal 58.

Figure 3A:
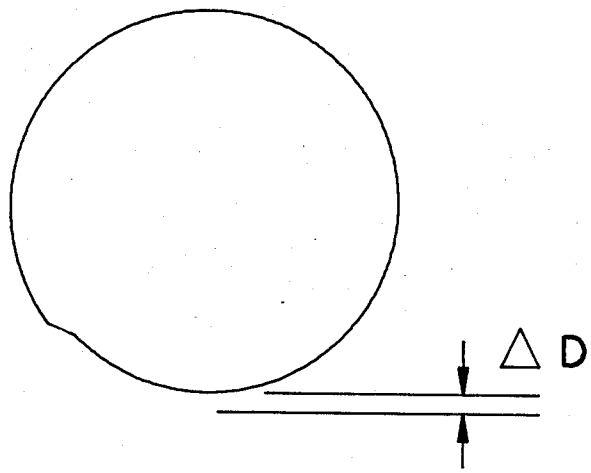
FIGS. 3(a) and 3(b) are respectively top and side views of a glass bottle showing various dimensions measured by the gauger according to the present invention.
Figure 3B:
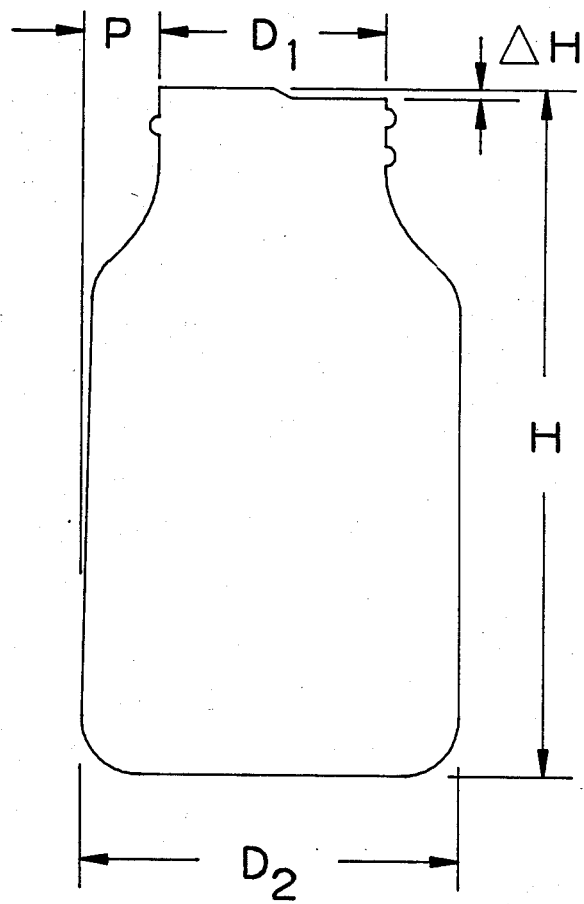

Referring now to FIGS. 3(a) and 3(b), there are shown bottom and side views of a glass bottle typical of the glassware produced by forming machine 30 and is representative of bottles 32, 34 and 36 shown in FIG. 1. Various critical dimensions appropriate to bottle inspections and measured by gauger 42 are shown in FIGS. 3(a) and 3(b). The height of a bottle is represented by dimension H. The perpendicularity is represented by P (less a predetermined offset). The neck diameter is represented by dimension $D_1$. The body diameter is represented by dimension $D_2$. The height variation of a bottle is represented by the dimension $\Delta H$.

The roundness of a particular bottle is represented by dimension $\Delta D$. $\Delta D$ can be determined by two separate and distinct methods. A set of mirrors can be used to provide several different views of a bottle to a single gauger 42. A body diameter measurement $D_2$ is taken for each of the views. Comparison of these multiple $D_2$ measurements provides a measure of the roundness cf a particular bottle. A perfectly round bottle will have identical body diameter $D_2$ measurements from all views. An out of round bottle will have different body diameter $D_2$ measurements from view to view.

A second method for measuring roundness requires the use of multiple gaugers. Multiple gaugers 42 are positioned about conveyor 38 so that each has a different view of a bottle on the conveyor. Each of gaugers 42 measures the body diameter $D_2$ from its own perspective. These separately taken measurements are compared with one another for an overall determination of roundness.

Genreally, all deimensions and measurements must be critically maintained. Measurement accuracy of within 0.01 inch is generally required. Based upon typical production numbers, a bottle inspection rate of 5–400 bottles/minutes is possible with bottle temperature within the range of 700°–1050° Farenheit.

Gauger 42 is a non-contact measurement system and measures solely by the use of optical signals passing through viewing window 48 (see FIG. 2). A collimated light source is utilized to generate a shadow image of each botle on conveyor 38 as it passes gauger 42.

The shadow image is sensed by a detector array 62 (shown in detail in FIG. 6). Detector array 62 converts the optical signals generated by the temporary interruption of the collimated light by a bottle into electrical signals. These electrical signals are processed by an electronic system and interpreted as measurements. The measurements are put into a digital format and stored for later use, tabulation, and analysis.

Referring now to FIG. 4, there is shown the presently preferred optical system utilizing three Fresnel lenses 78, 80 and 82. The image at an image plane 84 is reduced by 50% to facilitate the compact packaging of gauger 42. Three mirrors 86, 88 and 90 also help to reduce the size of the overall optical system. Lenses 78, 80 and 82 are advantageously cut to provide a 5 inch by 12 inch field of view. This optical system including three lenses and three mirrors provides a collimated beam generated by a light source 92 and reflected by a mirror 86. Bottle 76 on conveyor 38 passes through this collimated beam thereby interrupting it. The interruption is detected by detector array (not shown) located at image plane 84. Utilizing this optical system, a relatively large size collimator is required.

Alternative optical systems can be employed and are intended to fall within the scope of the present invention. Alternate optical systems are set forth in FIGS. 5 and 7.

Referring now to FIGS. 5 and 6, there are shown respectively a top cut-away and a front view of a portion of detector array 62. Detector array 62 is illustrated in conjunction with an alternate optical system utilizing a Fresnel reflector. However, detector array 62 is substantially identical no matter which type of optical system is selected.

Gauger 42 includes a light source system, a light sensing system, and an electronic system for processing signals produced by the light sensing system. The light source system includes a light source 64, a light emitting element 66, a fiber optic bundle for coupling light from the light source to the light emitting element, and a Fresnel reflector 70. Light emitted by light emitting element 66 propagates across conveyor 38 to Frensnel reflector 70 where it is reflected. Light reflected by Fresnel reflector 70 irradiates detectors 72 comprising a detector array 62. Detectors 72 are suitable photo diodes. However, photo transistors in combination with pull-up resistors and operational amplifiers voltage followers would be a suitable alternative.

Another suitable alternative would be the use of infra-red IR sensors for detectors 72 for generating signals directly responsive to the heat of a bottle and without the necessity of a collimated light source. When a bottle on conveyor 38 is at a sufficiently high temperature, infra-red detectors can detect the presence of a bottle without supplementary illumination as would otherwise be required and provided by light source 64. It should be noted however, that the input to the electronics from detectors 72 must be altered to match whatever type of detector is selected. When utilizing infra-red sensors, no light source system is required, but an optical imaging system is required which must be suitable for use at infra-red wave lengths. The infra-red radiation emitted by the glassware as it is being transported by conveyor 38 is detected. Computations are effected in the same way as they would be utilizing a light source and shadow image detector array. The output of detectors 72 are coupled to an electronic signal processing system 74 for interpretation.

As a bottle 76 is transported by conveyor 38 across the path of light reflected by Fresnel reflector 70 toward detector array 62, the light is interrupted for a period of time based upon the size of a bottle and the velocity of its conveyance on conveyor 38 so as to form a temporary shadow on detector array 62. These light interruptions are interpreted by electronic signal processing system 74 to realize the critical measurements shown in FIG. 3.

Another alternate optical system arrangement utilizes multiple light emitting elements from a single fiber optic bundle. Such an optical system iS shown in FIG. 7.

Referring now to FIG. 7, there is shown a top view of another alternate optical system utilizing a fiber optic bundle. This particular optical configuration avoids the necessity of using lenses and mirrors. Light is generated by a light source 97. A fiber optic bundle 98 carries this light under the conveyor 38 to an array of tubular light guides 99. Individual optic fibers carry light to each of tubular light guides 99 from fiber optic bundle 98. A small diaphragm 96 located at the end of each of tubular light guides 99 directs light from each optical fiber into a narrow beam. This "pin hole" arrangement produces a very sharp shadow edge without requiring critical alignment. The remaining elements are similar to those shown in FIGS. 4, 5 and 6.

Regardless of the particular type of optical system utilized, the detector array 62 including detectors 72 provides the signals to be interpreted as measurements. Detector array 62 is shown in greater detail in FIG. 8.

Referring now to FIG. 8, there is shown a detailed pictorial diagram of detector array 62 including a plurality of detectors 72. Particular detectors are noted by 72-N, such as 72-S1 and 72-S2 in the numbering scheme shown in FIG. 8. It is assumed for the purposes of this figure that the movement of a bottle 76 (not shown in this figure) is from left to right as indicated by the arrow. Eighteen sensors 72-S1 . . . 72-S18 are mounted on 0.250 inches centers in a fixed plane. Two additional sensors 72-V1 and 72-V2 are fixed in the viewing plane. A sub-array 100 of 10 detectors 72-A1 . . . 72-A10 is movable in the vertical direction. The position of sub-array 100 is controlled by a motor drive as will be further explained below. The measurement technique utilizing array 72 is better understood by reference to a side view of a bottle 76 being measured.

Referring now to FIG. 9, there is shown a side view of a typical bottle 76 being measured by gauger 42. Sub-array 100 including detectors 72-A1 . . . 72-A10 is utilized to measure bottle height H and height variation $\Delta H$ (see FIG. 3). Detectors 72-A1 . . . 72-A10, arranged with 6 mil spacing determine bottle height to within ±12 mils.

Once gauger 42 is in position, the overall displacement of sub-array 100 is adjusted to the approximate height of bottle 76. As bottle 76 passes in front of sub-array 100, continuous height measurements are made. These continuous height measurements can be used for checking for warped and leaning finishes (the "finish" is the upper portion of a bottle). A mirror image of the upper portion of a bottle can also be used to provide a second view of the finish. As bottle 76 interrupts light falling or detectors 72-A1 . . . 72-A10 the height of the bottle is determined by noting the particular detectors whose illumination is interrupted.

Bottle 76 diameter measurements are made using a velocity dependent scheme. The bottle velocity is determined by the time T that it takes for the leading edge of the bottle to pass between either pair of detectors 72-S2 and 72-V2 or 72-S4 and 72-V1. A counter counts clock pulse for the appropriate light interruption intervals. The time $C_T$ during which detector 72-SX senses bottle 76 is then used to determine bottle diameter according to the following formula:

$$\text{Diameter} = \frac{C_T}{T} \times S.$$

where S is the spacing between either sensors 72-S2 and 72-V2 or sensors 72-S4 and 72-V1. Other detectors can be used to measure distances across the bottle at different heights. The time during which these detectors detect the bottle is substituted for $C_T$ in formula (2) above. Eighteen vertical detectors 72-S1 . . . 72-S18 are located in a vertical line. This allows for the selection of a plurality of diameter measurements to be made in bottle testing. Diameter measurements to within 5 mils are possible using this scheme (not considering conveyor instability and vibration).

Bottle perpendicularity is also measured with the detector configuration shown in FIG. 8. The bottle's trailing edge time difference D as noted by detectors 72-A10 and 72-S1 is used to measure perpendicular offset in accordance with the following formula:

$$\text{Perpendicular Offset} = \frac{D}{T} \times S - H.$$

where H is the horizontal offset distance between detectors 72-A10 and 72-S1.

After bottles are measured each measurement is compared with a predefined standard for that measurement. Critical dimensions are evaluated on a scale of 1 to 5 as follows:

1—the dimension is too small (reject)
2—the dimension is marginally small
3—the dimension is at standard
4—the dimension is marginally large
5—the dimension is too large (reject).

The ratings of the most recently measured bottles are maintained in a data store for later recall. The accept-/reject decision for 24 hours of bottle production are also maintained. The bottles arrive sequentially from the sections 1–10 of forming machine 30 (shown in FIG. 1) so a particular section can be identified based upon the timing clock from forming machine 30 is provided.

An evaluation of either "1" or "5" for a particular dimension may be used as a trigger to generate a reject signal for activating reject plunger 44.

Figure 10:
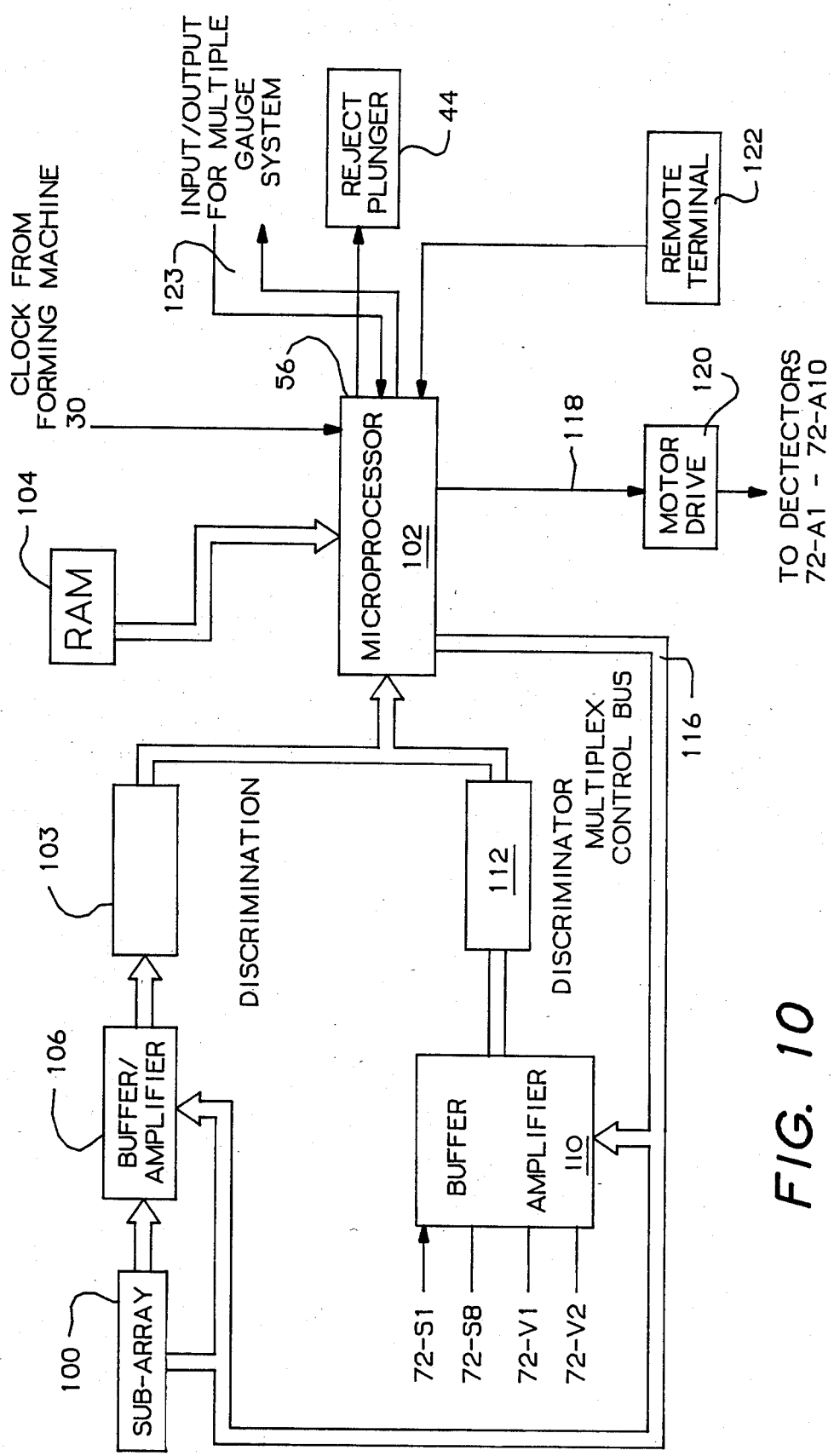
FIG. 10 is a block diagram of the electronic signal processor utilized in the gauger according to the present invention.

Referring now to FIG. 10 there is shown a block diagram of electronic system 64. In this presently preferred exemplary embodiment, electronic system 64 is a microprocessor-based system utilizing a microprocessor 102. However, it should be noted that the data processing functions of microprocessor 102 could be implemented by discrete, hard-wired components and logic circuits. Because the preferred embodiment is microprocessor implemented, flow charts are included so that the artisan of ordinary skill could generate the required software.

Microprocessor 102 is suitably an INTEL 8085 however, the data processing functions performed thereby could be implemented by any other commercially available microprocessor with suitable alterations made for the particular configuration selected. Associated with microprocessor 102 is a random access memory (RAM) 104. RAM 104 serves as the data store for maintaining a look up table for measurements comparisons and for maintaining records of measurements taken for various production runs of glassware. RAM 104 is suitably a CMOS, battery supported memory. Battery support insures that data is not lost in case of power fluctuation or power failure.

Data from detectors 72 within sub-array 100 are coupled through a buffer/amplifier 106 to a discriminator 108. The outputs of detectors 72-S1 . . . 72-S18 and 72-V1 and 72-V2 are coupled through a buffer amplifier 110 to a discriminator 112. The output of discriminators 108 and 112 are multiplexed onto the common data lines 114 of microprocessor 102. A multiplex control bus 116 coupled to buffer amplifiers 106 and 110 provide appropriate multiplexing of the signals from sub-array 100 and the remaining detectors 72 thus, input/output circuitry is minimized. Microprocessor 102 provides a motor control line signal on a motor control line 118. This signal controls the up/down motion of sub-array 100 through a motor drive 120. Microprocessor 102 provides reject signal at terminal 56 for coupling to reject plunger 44 each time measurements of a particular piece of glassware indicate it is outside of minimally acceptable tolerance (rate 1 or 5). In addition, microprocessor 102 interfaces with a remote terminal 122 which suitably includes a display such as a CRT and printer for allowing user interaction. A printer allows the user to generate reports such as shown in FIGS. 17 and 18. The actual data processing function is controlled by firmware established within microprocessor 102. Various flow charts are included to fully set forth the particular data processing functions that take place. Primarily, three separate and distinct functions occur. Firstly, individual bottles are measured. Secondly, these measurements are analyzed and categorized. Thirdly, interactive communication is established with the user through remote terminal 122.

Figure 11:
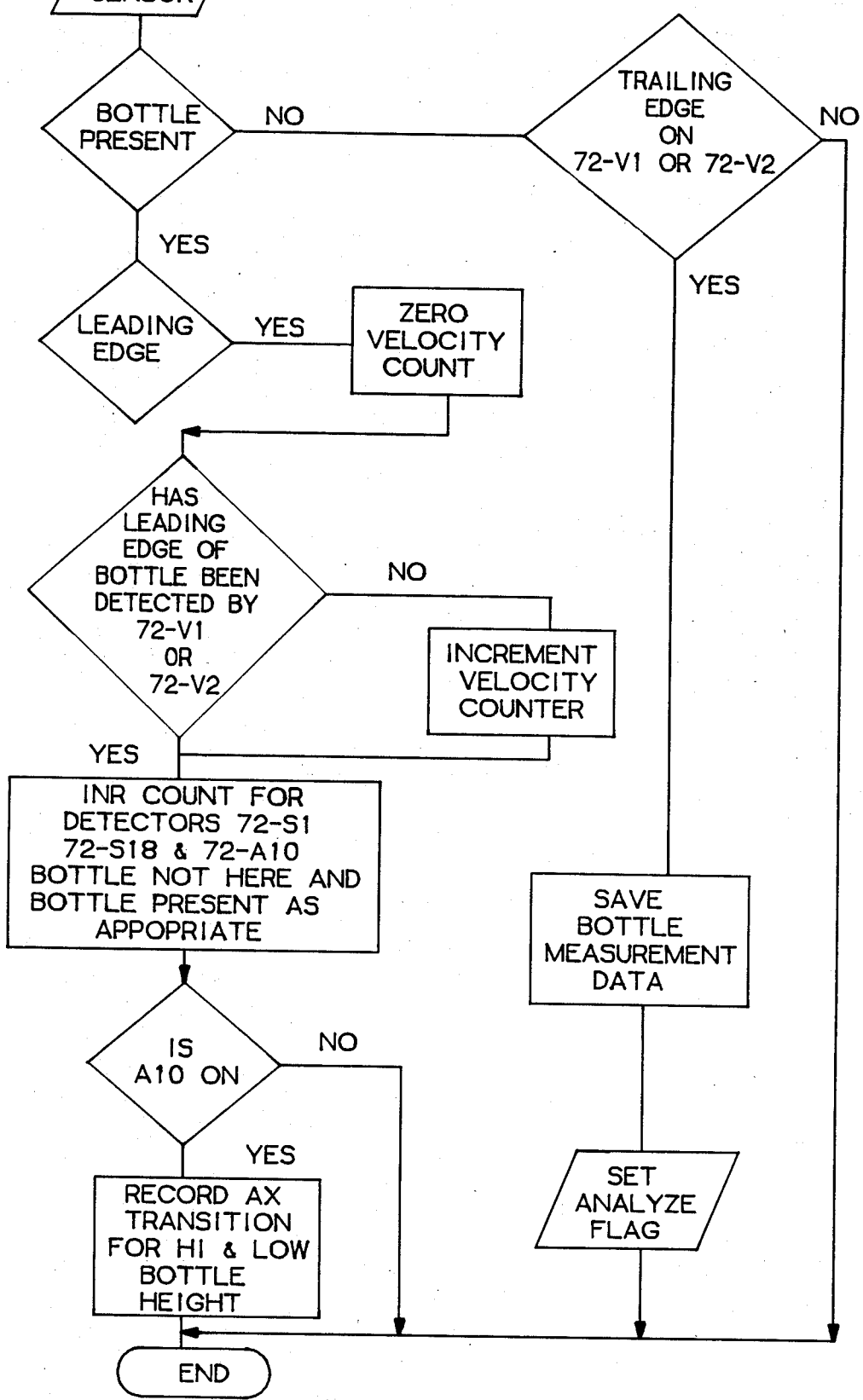
FIG. 11 is a flow chart of the bottle measurement task performed by the electronic signal processor.

Referring now to FIG. 11, there is shown a flow chart of the bottle measurement task performed by microprocessor 102 and its associated elements. Each of detectors 72 is read in sequence at a 5 kHz rate. Thus, the flow chart begins with a 200 microsecond interrupt. As previous stated, bottle diameter measurements are made utilizing a velocity dependent scheme. The velocity of a bottle is determined by the time it takes for the leading edge of a bottle to pass between two sensors, namely sensors 72-S2 to 72-V2 or 72-S4 to 72-V1. The time during which detector 72-S1 senses a bottle is then used to indirectly determine bottle diameter according to formula (1) above.

Sensors 72-S1 . . . 72-S18 and 72-A10 are utilized to measure distances across the bottle. There is a counter associated with each sensor so that the time interval during which each sensor detects a bottle can be used in the appropriate formula to determine bottle diameter. In the presently preferred exemplary embodiment, the firmware associated with microprocessor 102 selects three separate and distinct diameters measurements to be made by three different sensors 72-N from among sensors 72-S1 . . . 72-S18.

In order to measure bottle perpendicularity, a bottle's trailing edge time difference between that sensed by detector 72-A10 and that sensed by detector 72-S1 is noted and utilized to determine perpendicularity offset in accordance with formula (3) previously set forth.

The bottle roundness measurements are obtained by measuring the diameter from a plurality of different views of a bottle. A technique for measuring bottle roundness utilizing only one gauger 42 uses mirrors to provide several views (from different angles) of the bottle being measured. Diameter measurements are taken in succession from each of these views. These separate diameter measurements are then compared. A perfectly round bottle will have identical diameter measurements from all views. Out of round bottles will have differing diameter mesurements, the more extreme the difference in measurement indicating the more out of round bottle.

A second technique for measuring bottle roundness utilizing multiple gaugers 42. Multiple gaugers 42 are positioned about conveyor 38 and arranged so as to each have a view of a bottle that is different the view of the other gaugers. Each of the multiple gaugers independently measures the diameter of the same bottle. These independent diameter measurements are then compared to determine roundness.

After all raw data related to light interruption time intervals has been taken an "analyze" flag is set and control is returned to an executive routine.

Figure 12A:
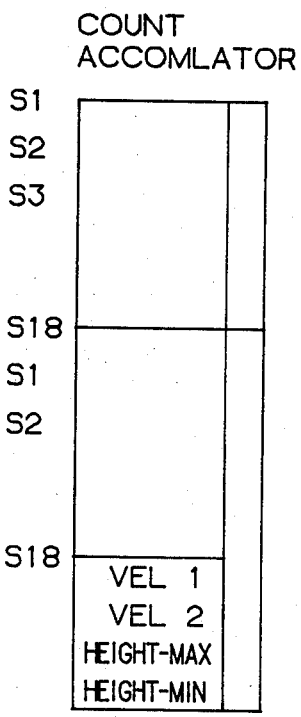
FIGS. 12a–12c are a diagrammatic representation of the manner in which data representing bottle measurements is stored
Figure 12B:
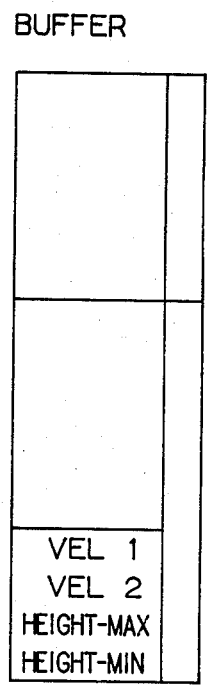
Figure 12C:
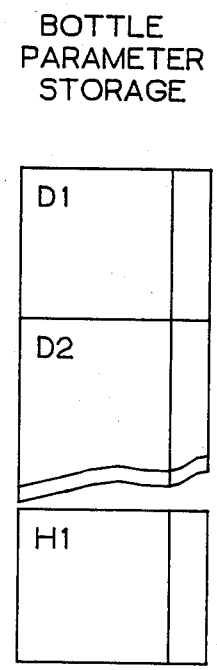

Referring now to FIGS. 12(a), (b), and (c), there are shown diagrammatic representations of the manner in which raw data collected from each of detectors 72 is stored pending the analyzing task. FIG. 11(a) shows a count accumulator area of memory within random access memory 104 which temporarily stores the tally of counters associated with each of detectors 72 (one counter associated with each detector). Bottle height maximum and minimum are recorded in the bottom two cells of the count accumulator memory block. The tally in the counter accumulator memory block is incremented for particular detectors 72 as the bottle is passing, thereby. After a bottle passes the detection area and counters are no longer being incremented all the count information is transferred to a buffer area of memory shown in FIG. 11(b), then the analyze flag is set (see FIG. 10). At this point bottle inspection is completed and the data accumulated must be analyzed.

A separate block of RAM 104 memory known as bottle parameter storage and shown in FIG. 11(c) is dedicated to bottle parameter storage. This area contains predefined "ideal" measurement data and is used for comparison with the data stored in the buffer area of memory. The 1-5 value associated with each measurement is assigned based upon this data. Bottle parameter storage includes criteria for bottle diameter at various height, indicated by D1, D2, etc. It further includes data related to acceptable heights indicated by H. After all raw data has been collected and stored and the "analyze" as been set, the data is analyzed. A flow chart of the analysis routine executed by microprocessor 102 as set forth in FIG. 13.

Figure 13:
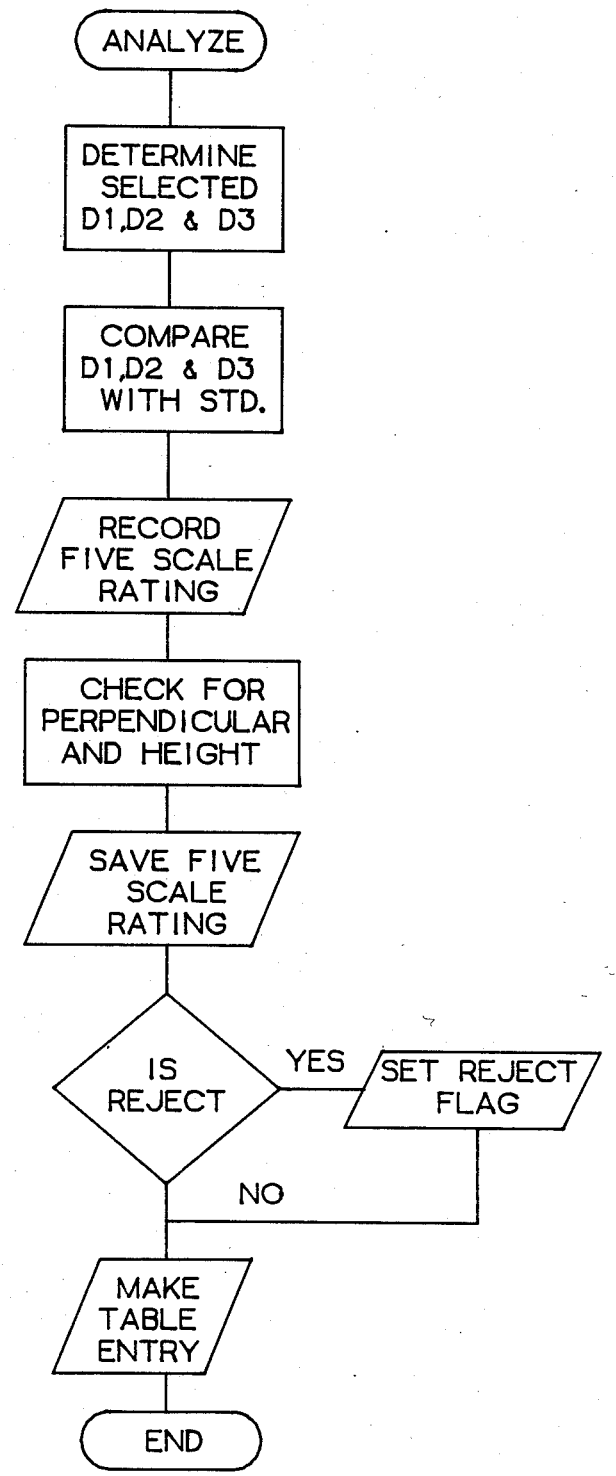
FIG. 13 is a flow chart of the analysis task performed by the electronic signal processor after measurements have been made.

Referring now to FIG. 13, there is shown a flow chart of the analysis routine that is executed after all raw data bottle measurements have been taken. Three specific diameter measurements are compared with ideal diameter measurements stored in the bottle parameters storage region of memory. The 5 scale rating previously discussed is applied to these diameter measurements. Then perpendicularity and height are checked and the 5 scale rating again applied. If a particular bottle is outside minimum tolerance (rating of 1 or 5) a reject flag may be set. This flag will at a later time cause reject plunger 44 to be activated. Regardless of whether or not a reject flag is set, table entries are made of the ratings assigned to each measurement. Such data is stored for a predetermined number of measured bottles for later use. This data can be used to generate a hard copy print out or display summarizing the quality of a particular production run from forming machine 30. This data can be correlated from the individual sections of forming machine 30 so that it will be immediately apparent to the user whether a particular section of forming machine 30 is malfunctioning or is in need of adjustment. The results of the data analysis are stored as shown in FIGS. 14(*a*), (*b*), and (*c*).

Referring now to FIGS. 14(*a*), (*b*), and (*c*), there is shown a pictorial representation of various areas of memory and the format for data storage. In essence, the measurements form a statistical base for analysis of a particular production run.

After a bottle is analyzed the results of the inspection are stored in a LIFO buffer, shown in FIG. 14(*a*). The buffer stores the 1024 most recent readings. Each 16 bit word in the buffer contains the status of one bottle. The data is packed as shown in the figure. A tabulation of good and bad bottles is also kept as shown in FIG. 14(*a*). Each bottle is counted by section as either good or bad as shown in FIG. 14(*b*). A bottle is considered bad if any of its measured parameters are graded as 1 or 5 and the inspection device is initialized to reject those categories. This data is accumulated for a specified period of time i.e., a shift or eight hours. The counts are then stored in a history file shown in FIG. 14(*c*). The present data file is cleared and tabulation begins again.

Control of the overall function of gauger 42 is via a serial communication link. Set up information describing bottle parameters, tolerances and whether or not a particular parameter rating 1–5 should reject a bottle are loaded into RAM 104 through remote terminal 122. System initialization and configuration information is similarly loaded before any measurements are taken. The positioning of detectors 72-A1 . . . 72-A10 as controlled by motor drive 120 is also preset via user interaction through remote terminal 122. Remote terminal 122 not only enters information into microprocessor 102 but serves as a vehicle for readback of stored information to the user. Machine status job information and air conditioners are all accessible through remote terminal 122.

Figure 15:
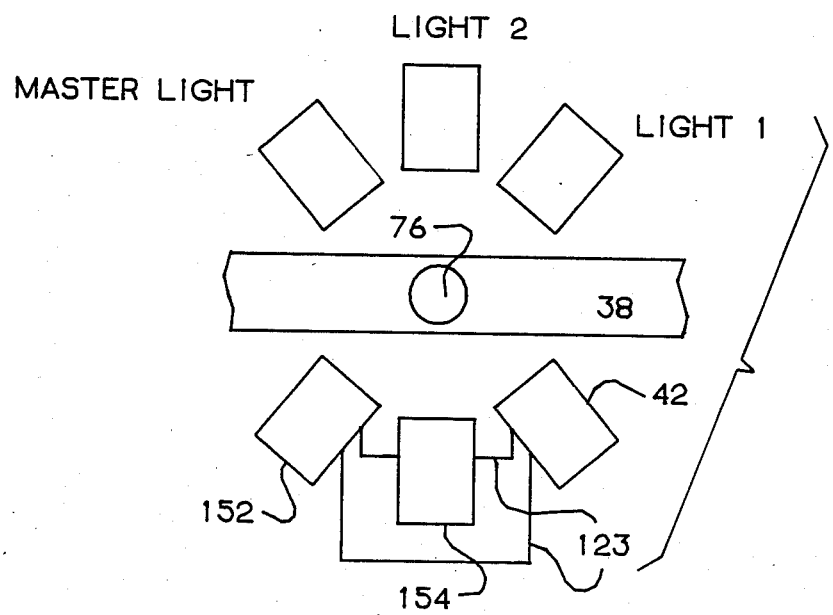
FIG. 15 is a top pictorial view of a multiple gauger arrangement.
Figure 16:
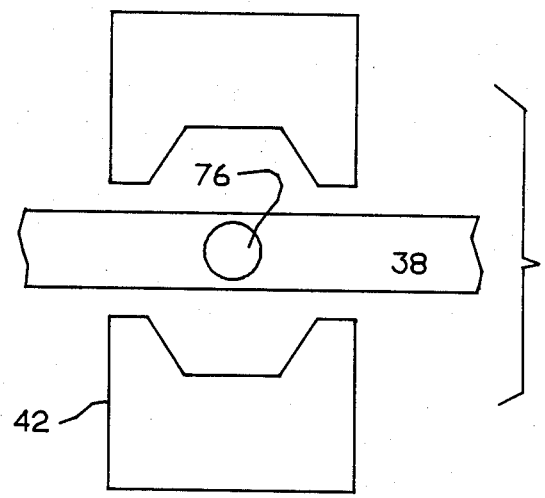
FIG. 16 is a top pictorial representation of a multiple view arrangement utilizing a single gauger.

Referring now to FIGS. 15 and 16, there are shown top view pictorial representations of two different roundness measurement arrangements. Roundness measurements require two or more side views of a bottle. The first such arrangement employs multiple gaugers as shown in FIG. 15. One of the gaugers is designated a master gauger 42. Associated with master gauger 42 are slave gaugers 152 and 154. Master gauger 42 coordinates all gauging activites. After a bottle is measured by each gauger, master gauger 42 requests data from each slave unit. This data is transferred to microprocessor 102, associated with master gauger 42, by an eight-bit data link 123. Data link 123 is shown in the block diagram of the electronic system set forth in FIG. 10. Master gauger 42 averages the height measurements from each of the three gaugers and applies the "1" . . . "5" quality factor scale. The neck and body diameter measures are similarly averaged and graded. The height variation measurement is not averaged. A high and low reading for all measurements is found and graded. Perpendicularity is graded based upon the worst of case data reported from any of gaugers 42, 152 and 154.

Roundness is measured as the maximum difference between any two gauger diameter measurements. A grading of 3, 4 or 5 is applied to these measurements. A grade of 3 designates minimum variation among the measurements taken by gauger 42, 152 and 154. A grading of 4 represents some variation among the individual gauger measurements and a grading of 5 represents excessive variations among them.

A single system multi-view gauger can also be used to check for roundness. Such a system is illustrated in FIG. 16. In this arrangement, a mirror provides multiple views for a single gauger 42. This sytem involves less redundancy. Height and diameter measurements need not be computed for each view. Thus, one electronic system can be utilized for all views. Perpendicularlity and roundness data are calculated and graded utilizing the approach set forth in the multiple gauger system.

Data stored in the various areas of RAM 104 can be formatted so as to be printed out in the form of graph and records reports as set forth in FIGS. 17 and 18 respectively. On the graph report set forth in FIG. 17, each line on the page lists the test results for one bottle. The first numbers under each of the five right most columns indicate the number of a five step scale for particular measurement. If a "1" or "5" rating is to reject a bottle, an "R" is printed at the appropriate point on the graph report. For example, the first bottle from section 1 is on target for all measurements except for D2. The fifth bottle inspected was rejected based upon two separate measurements.

It is contemplated that four different graph reports can be requested by the user:
1. List each bottle produced on section N.
2. List each bottle as produced.
3. List defective bottle for section N.
4. List defective bottles as produced.

It is further contemplated that each graph report will continue to print out in a scrolling mode until an instruction to stop has been entered.

It is also contemplated that an autograph mode be available to the user. This autograph mode would cause a sequential scanning through each section. All glassware produced by the section scanned is displayed for 10 seconds. This process continues new section's test listings. Until a reject is produced in one of the machines. Ten bottles from this section are then listed. The listings return back to the 10 second scanning mode only after ten non-defective bottles are produced by the section judged to be faulty. The regular scan sequence would then continue.

A typical records report is shown in FIG. 18. This report is included in order to determine long term trends in manufacturing. In essence, it summarizes rejects and good wares.

Therefore, it is apparent that there has been provided a method and apparatus for the non contact gauging of glasswre produced at the "hot end" of a glass plant. The system is capable of rejecting bottles having dimension outside of a predetermined tolerance range and provides inspection information for the close loop control of forming machine.

Other embodiments and modifications of the present invention will be apparent to those of ordinary skill in the art having the benefit of the teachings presented in the foregoing description and drawings. It is therefore to be understood that this invention is not to be unduly limited and such modifications are intended to be included within the scope of the appended claims.

What is claimed is:

1. A non-contact gauger for measuring the diameter of an article of manufacture that is being conveyed comprising:
   means for sensing the transit time of a first edge of the article of manufacture from a first predetermined position to a second predetermined position and for generating a velocity signal proportional thereto;
   means for detecting the interval of time associated with the passage of the first edge of the article of manufacture past a third predetermined position and the passage of a second edge of the article of manufacture past the third predetermined position and for generating a time interval signal proportional thereto; and
   means for combining the velocity and time interval signals to generate diameter data proportional to the diameter of the articles of manufacture.

2. A non-contact gauger according to claim 1 wherein said third predetermined position and said first predetermined position are in the same vertical plane.

3. A non-contact gauger according to claim 1 wherein said means for sensing comprises a first light sensitive element for sensing the first edge of the article of manufacture at the first predetermined position and a second light sensitive element for sensing the first edge of the article of manufacture at the second predetermined position.

4. A non-contact gauger according to claim 1 further including a first data store for storing the diameter data.

5. A non-contact gauger according to claim 4 further including a second data store for storing predefined criteria representative of desired diameter data; and
   means for comparing the data in said first data store with said criteria in said second data store and for assigning a quality factor based upon the comparison.

6. A non-contact gauger according to claim 1 wherein said means for sensing includes a light source for illuminating first and second light sensitive elements at said first and second predetermined positions, respectively, said light sensitive elements sensing the interruption of said light by the first edge of the article of manufacture.

7. A non-contact gauger according to claim 1 wherein said means for detecting the interval of time includes a light source; and a light sensitive element for receiving a light beam generated by said light source, said light sensitive element sensing the interruption of light caused by the first edge of the article of manufacture passing between the light source and light sensitive element at the third predetermined position and further sensing the return of light impinging upon said light sensitive element when the second edge of the article of manufacture passes the third predetermined position.

8. A non-contact gauger according to claim 1 wherein said means for sensing includes at least one infra-red sensor for detecting radiation from the article of manufacture.

9. A non-contact gauger according to claim 1 wherein said means for detecting includes at least one infra-red sensor for sensing radiation from said article of manufacture.

10. A method for non-contact measurement of the diameter of an article of manufacture which is being conveyed comprising the steps of:
    sensing the transit time of a first edge of the article of manufacture from a first predetermined position to a second predetermined positon and generating a velocity signal proportional thereto;
    detecting the interval of time associated with the passage of the first edge of the article of manufacture past a third predetermined position and the passage of a second edge of the article of manufacture past the third predetermined position and generating a time interval signal proportional thereto; and
    combining the velocity and time interval signals to generate diameter data proportional to the diameter of the article of manufacture.

11. A non-contact gauger for measuring the perpendicularity of an article of manufacture in transit on a conveyor comprising:
    first means for sensing when a first point along an edge of said article of manufacture reaches a vertical plane defined by a first predetermined position along the conveyor and generating a first signal responsive thereto;
    second means for sensing when a second point along said edge of said article of manufacture reaches a vertical plane defined by a second predetermined position along the conveyor and generating a second signal responsive thereto; and
    means for measuring the interval of time between the first and second signals and generating a perpendicularity signal proportional to the time interval whereby said perpendicularity signal is a measure of the perpendicularity of the article of manufacture.

12. A non-contact gauger according to claim 11 wherein said first means for sensing comprises means for sensing the interruption of a beam of light.

13. A non-contact gauger according to claim 11 wherein said second means for sensing comprises means for sensing the interruption of a beam of light.

14. A non-contact gauger according to claim 11 wherein said first means for sensing comprises first means for sensing radiation from the article of manufacture.

15. A non-contact gauger according to claim 14 wherein said first means for sensing radiation comprises means for sensing infra-red radiation.

16. A non-contact gauger according to claim 11 wherein said second means for sensing comprises second means for sensing radiation from the article of manufacture.

17. A non-contact gauger according to claim 16 wherein said second means for sensing radiation comprises means for sensing infra-red radiation.

18. A method for non-contact measurement of the perpendicularity of an article of manufacture in transit on a conveyor comprising the steps of:
    sensing when a first point along an edge of said article of manufacture reaches a vertical plane defined by a first predetermined position along the conveyor and generating a first signal responsive thereto;
    sensing when a second point along said edge of said article of manufacture reaches a vertical plane defined by a second predetermined position along the conveyor and generating a second signal responsive thereto; and measuring the interval of time between the first and second signals and generating a perpendicularity signal prportional to the time interval whereby said perpendicularity signal is a measure of the perpendicularity of the article of manufacture.

19. A method for measuring the roundness of a piece of glassware in transit on a conveyor comprising the steps of:

measuring the body diameter of the glassway from each of several views, said measuring step from each of said several views including sensing the transit time of a first edge of said piece of glassware from a first predetermined position to a second predetermined position and generating a velocity signal proportional thereto;

detecting the interval of time associated with the passage of the first edge of the piece of glassware past a third predetermined position and the passage of a second edge of the piece of glassware past the third predetermined position and generating a time interval signal proportional thereto; and combining the velocity and time interval signals to generate diameter data proportional to the diameter of the piece of glassware from each of said several views; and comparing the diameters measured in each of said views to determine the roundness of the piece of glassware.

20. A non-contact gauger for measuring the roundness of an article of glassware in transit on a conveyor comprising:

mirror means for generating a plurality of optical views of the article of glassware;

means for measuring the diameter of the article of glassware in each of said plurality of optical views, said measuring means including means for sensing the transit time of a first edge of the article of glassware from a first predetermined position to a second predetermined position and for generating a velocity signal proportional thereto;

means for detecting the interval of time associated with the passage of the first edge of the article of glassware past a third predetermined position and the passage of a second edge of the article of glassware past the third predetermined position and for generating a time interval signal proportional thereto; and means for combining the velocity and time interval signals to generate diameter data proportional to the diameter of the article of glassware at each of said plurality of optical views; and means for comparing the diameters measured in each of said plurality of optical views whereby roundness is determined.

21. A system for measuring the roundness of an article of glassware in transit on a conveyor comprising:

a plurality of non-contact gauging means for measuring the diameter of the article of manufacture from a plurality of views, each of said gauging means including means for sensing the transit time of a first edge of the article of glassware from a first predetermined position to a second predetermined position and for generating a velocity signal proportional thereto;

means for detecting the interval of time associated with the passage of the first edge of the article of glassware past a third predetermined position and the passage of a second edge of the piece of glassware past the third predetermined position and for generating a time interval signal proportional thereto; and means for combining the velocity and time interval signals to generate diameter data proportional to the diameter of the article of glassware at each of said plurality of optical views; and means for comparing the diameter measurements made by each of said gauging means for determining the roundness of said articles of glassware.

* * * * *